United States Patent [19]

Iwata et al.

[11] Patent Number: 5,171,046
[45] Date of Patent: Dec. 15, 1992

[54] ASSEMBLY COMPOSED OF HARD MEMBER AND SOFT TUBE FOR MEDICAL USE

[75] Inventors: Minoru Iwata, Miyoshi; Hideyuki Yamashita, Shimane, both of Japan

[73] Assignee: Japan Medical Supply Co., Ltd., Hiroshima, Japan

[21] Appl. No.: 562,567

[22] Filed: Aug. 3, 1990

[51] Int. Cl.⁵ ............................................. F16L 33/00
[52] U.S. Cl. ................................... 285/331; 285/255; 285/259; 285/240; 285/256; 285/382
[58] Field of Search ............. 285/331, 255, 239, 259, 285/240, 382, 256, 909, 423; 29/451, 450

[56] References Cited

U.S. PATENT DOCUMENTS

| | | | |
|---|---|---|---|
| 909,003 | 1/1909 | Lepage | 285/259 X |
| 1,228,549 | 6/1917 | Furduy | 285/255 X |
| 1,314,235 | 8/1919 | Adkins | 285/331 X |
| 2,292,752 | 8/1942 | Gee | 285/240 |
| 2,805,088 | 9/1957 | Cline et al. | 285/239 |
| 3,695,632 | 10/1972 | Kruse et al. | 285/255 |
| 4,521,041 | 6/1985 | Cox et al. | 285/909 X |
| 4,562,915 | 1/1986 | DiAntonio | 285/238 X |
| 4,925,216 | 5/1990 | Steer | 285/3 |

FOREIGN PATENT DOCUMENTS 63-283651 11/1988 Japan.
19995 of 1908 United Kingdom ................ 285/239

Primary Examiner—Randolph A. Reese
Assistant Examiner—Timothy Aberle
Attorney, Agent, or Firm—Cushman, Darby & Cushman

[57] ABSTRACT

An improved assembly, composed of a hard member and a soft tube fitted onto the hard member, for medical uses is formed with a plurality of projections on the side wall of a flange of the hard member. The projections project toward the soft tube side to firmly hold the foremost end part of the soft tube between the projections and a fitting portion of the hard member in a clamped state when the soft tube is fitted onto a fitting portion of the hard member. The foremost end surface of the soft tube may slantwise be cut to define a certain angle relative to the center axis of the assembly such that the foremost end part of the soft tube comes in tight contact with the side wall of the flange when the soft tube is fitted onto the fitting portion of the hard member. The soft tube may be formed with a plurality of cutouts which are arranged along the periphery of the foremost end surface of the soft tube in a spaced relationship. Each cutout preferably exhibits a V-shaped contour which defines a certain opening angle symmetrically relative to the center axis of the assembly.

3 Claims, 2 Drawing Sheets

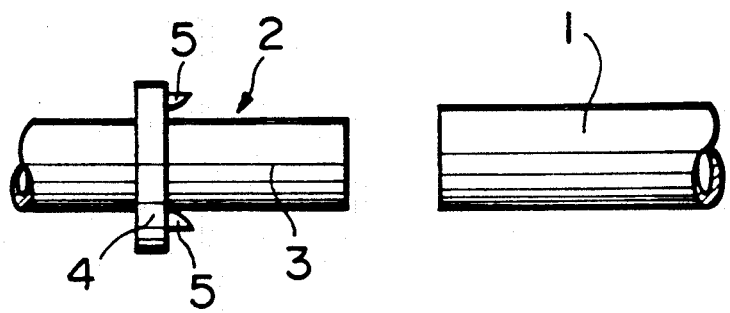
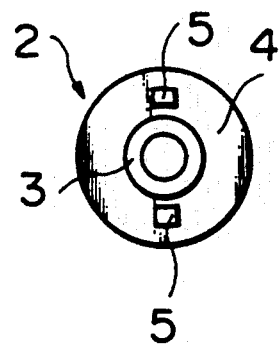
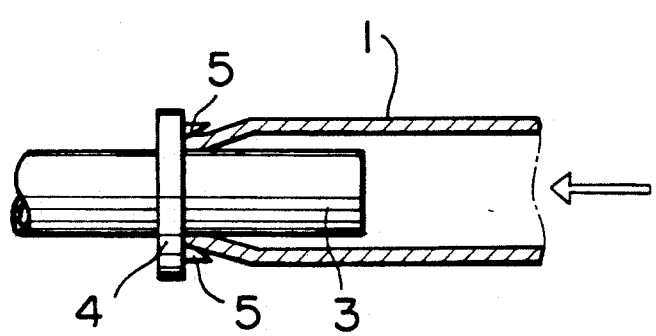
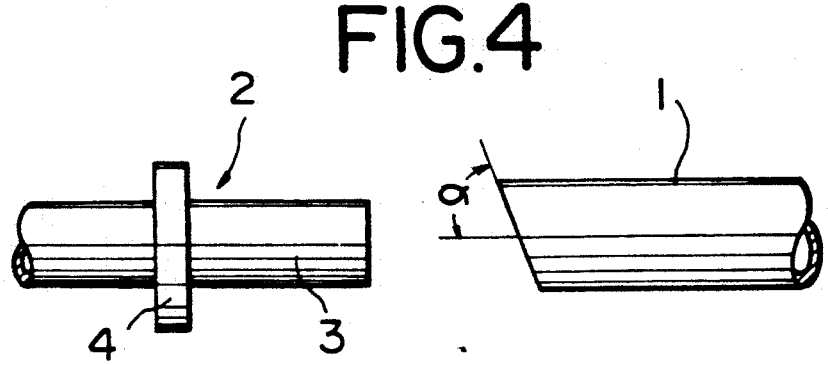

ASSEMBLY COMPOSED OF HARD MEMBER AND SOFT TUBE FOR MEDICAL USE

BACKGROUND OF THE INVENTION

1. Field Of The Invention

The present invention relates generally to an assembly composed of a hard member and a soft tube fitted onto the hard member for medical applications. More particularly, the present invention relates to an improvement in the assembly of soft tubes and hard members often used as essential components for blood transfusion sets, infusion sets or the like medical devices.

2. Description Of The Prior Art

Many soft tubes each molded of soft synthetic resin, e.g., polyvinyl chloride or the like material have been heretofore used for blood transfusion sets, infusion sets or the like medical devices. Each soft tube is practically used by connecting it to another component, in the form of a hard member, to provide an assembly composed of the hard member and the soft tube for use in a medical device. When such a soft tube, molded of soft polyvinyl chloride or the like material, is connected to the hard member, molded of hard synthetic resin, e.g., polyethylne, polypropylene or the like material, a firm connection is usually carried out by a manual simple fitting operation, because a suitable adhesive employable for the joining of soft and hard synthetic resin is not available at present. In practice, a tight fitting operation is physically performed by dimensioning the inner diameter of the soft tube to be appreciably smaller than the outer diameter of the hard member and forcibly fitting the soft tube onto a fitting portion of the hard member in opposition to a contractive force and a frictional force generated by contraction of the soft tube.

Over time, a slight loosening appears between the soft tube and the hard member. This often leads to trouble in that the soft tube is undesirably disconnected from the fitting portion of the hard member due to reduction of the tightening force which has been induced therebetween.

To solve the foregoing problem, the inventors closely observed disconnection malfunctions as described above. As a result of their observations, they found that disconnections occurred very easily when the close contact region between the soft tube and the hard member disappeared.

FIG. 6 is a side view of a typical conventional assembly composed of a hard member 2 and a soft tube 1 fitted onto a fitting portion 3 of the hard member 2 for medical use. FIG. 7 is a fragmentarily exploded side view of the assembly in FIG. 6. When an intense thrusting force is imparted to the soft tube 1 which has been fitted onto the fitting portion 3 of the hard member 2 under the influence of a reduced magnitude of tightening force, as shown in FIG. 6, the foremost end of the soft tube 1 comes in close contact with the side wall of a flange 4. As a result, the diameter of the foremost end of the soft tube 1 is enlarged with an axial compressive force (see FIG. 7). Consequently, the close contact region between the soft tube 1 and the hard member 2 disappears. If the soft tube 1 is pulled rearwardly to a slight extent while the foregoing state is maintained, disconnection occurs easily with the soft tube 1 because no tightening force exists. In particular, when the conventional assembly is heated during sterilization, the tendency of disconnection of the soft tube 1 becomes remarkably increased.

In view of such malfunctions, it has been proposed that the diameter of the fitting portion 3 of the hard member 2 be dimensioned to become larger towards the flange 4, so as to allow the tightening force to increase correspondingly. Although the tightening force has been increased to some extent with this arrangement a sufficient improvement has not been obtained with this proposal with respect to prevention of undesirable disconnection from occurring with the soft tube 1.

In addition, another proposal has been disclosed in official gazette of Japanese Laid-Open Patent NO. 283651/1988. According to this prior invention, a lower cap for the drip chamber of an infusion set is connected to a soft tube with an improved structure for the purpose of avoiding the problem of undesirable disconnection of the soft tube. However, the improved structure is complicated and therefore the resultant assembly composed of the lower cap and the soft tube is fabricated with many difficulties.

Additionally, it was disclosed that a member made of polyvinyl chloride could be adhered to a member made of polyolefin by using a chlorinated polyolefin-based adhesive. However, once the hard member is coated with this adhesive, it becomes very difficult to insert the hard member into the soft tube because of the increased frictional force. Therefore, this proposal can not be put to practical use.

To substantially improve the conventional assembly composed of a hard member and a soft tube fitted onto the hard member for medical use, the inventors conducted a number of development works and determined that a plurality of projections formed on a flange of the hard member were very effective for preventing the soft tube from being disconnected from the hard member. Further, the inventors found out that particular configurations employed for the soft tube were likewise very effective for the same purpose.

SUMMARY OF THE INVENTION

The present invention has been made with the foregoing background in mind.

An object of the present invention is to provide an assembly composed of a hard member and a soft tube fitted onto the hard member for medical uses, where a malfunction of disconnection of the soft tube from the hard member does not occur.

Another object of the present invention is to provide an assembly composed of a hard member and a soft tube fitted onto the hard member for medical uses, wherein the assembly is easily fabricated at inexpensive cost.

To accomplish the above objects, there is provided according to one aspect of the present invention an assembly composed of a hard member and a soft tube fitted onto the hard member for medical uses, the hard member being molded of hard synthetic resin and including a flange and the soft tube being molded of soft synthetic resin, wherein the flange is formed with a plurality of projections which are arranged along a common circle in a spaced relationship, the projections projecting toward the soft tube side to firmly hold the foremost end part of the soft tube between the projections and the fitting portion of the hard member in a clamped state, when the soft tube is fitted onto the fitting portion of the hard member and then the foremost end surface of the soft tube comes in close contact with the side wall of the flange of the hard member.

Further, according to another aspect of the present invention, there is provided an assembly composed of a hard member and a soft tube fitted onto the hard member for medical uses, the hard member being molded of hard synthetic resin and including a flange and a fitting portion on which the soft tube is fitted and the soft tube being molded of soft synthetic resin, wherein a part or the whole part of the foremost end surface of the soft tube does not extend in parallel with the side wall of the flange of the hard member.

In practice, the foremost end surface is slantwise cut to define a certain inclination angle relative to the center axis of the assembly.

The soft tube may be formed with a plurality of cutouts along the foremost end surface thereof in a spaced relationship.

It is desirable that each cutout exhibits a V-shaped contour which defines a certain opening angle symmetrically relative to the center axis of the assembly.

Other objects, features and advantages of the present invention will become apparent from the following description which has been made with reference to the accompanying drawings.

BRIEF DESCRIPTION OF THE DRAWINGS

The present invention is illustrated in the following drawings in which:

FIG. 1 is a side view of an assembly composed of a hard member and a soft tube fitted onto the hard member for a medical uses in accordance with a first embodiment of the present invention in a disassembled state;

FIG. 2 is an end view of the assembly in FIG. 1 as seen in the axial direction.

FIG. 3 is a fragmentarily exploded side view of the assembly in FIG. 1.

FIG. 4 is a side view of an assembly composed of a hard member and a soft tube fitted onto the hard member for medical uses in accordance with a second embodiment of the present invention in a disassembled state;

DESCRIPTION OF THE PREFERRED EMBODIMENTS

Now, the present invention will be described in detail hereinafter with reference to the accompanying drawings which illustrate preferred embodiments thereof.

FIG. 1 is a side view which illustrates the disassembled components of the assembly of a hard member and a soft tube fitted onto the hard member for medical uses (hereinafter referred to simply as an assembly) in accordance with a first embodiment of the present invention. FIG. 2 is an end view of the assembly as seen in the axial direction.

Figure 6:
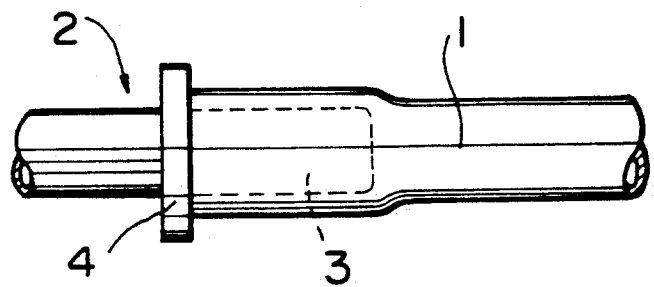
FIG. 6 is a side view of a conventional assembly composed of a hard member and a soft tube fitted onto the hard member for a medical uses.
Figure 7:
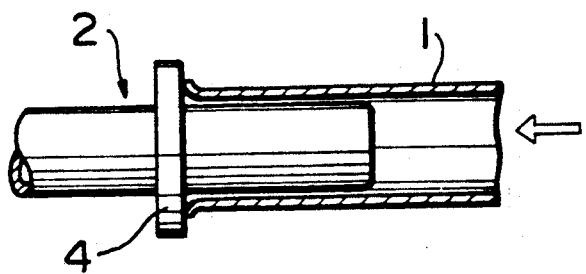
FIG. 7 is a fragmentarily exploded side view of the conventional assembly in FIG. 6.

The assembly of the present invention comprises a soft tube 1 molded of soft synthetic resin, e.g., soft polyvinyl chloride, ethylene-vinyl acetate copolymer or the like material and a hard member 2 molded of hard synthetic material, e.g., polyethylne, polypropylene or the like material. The hard member 2 includes a fitting portion 3 and a flange 4 so that the foremost end of the soft tube 1 comes in close contact with the side wall of the flange 4 in the same manner as the conventional assembly which has been described above with reference to FIGS. 6 and 7.

According to the present invention, the flange 4 is formed with a plurality of projections 5 (two projections in the shown embodiment). As will be readily apparent from FIG. 3, when the soft tube 1 is fitted onto the fitting portion 3 of the hard member 2, the foremost end of the soft tube 1 is brought in tight contact with the side wall of the flange 4 in cooperation with the projections 5 much more than the conventional assembly. Specifically, as a certain intensity of squeezing force is imparted to the soft tube 1, the foremost end of the soft tube 1 is tightly clamped between the fitting portion 3 of the hard member 2 and the projections 5, thereby a frictional contact state therebetween which reliably prevents the soft tube 1 from being undesirably disconnected from the fitting portion 3 of the hard member 2.

In this embodiment, the flange 4 is formed with two projections 5. However, the present invention is not limited to only two projections. The number of projections 5 and the size of each projection 5 may be determined, as desired. It should be noted, however, that if a single projection is formed on the flange 4, a clamping force is reduced excessively. Therefore, it is preferable that the flange 4 is formed with at least two projections 5 which are arranged along a common circle in a spaced relationship.

FIG. 4 is a side view which illustrates an assembly composed of a hard member and a soft tube fitted onto the hard member in accordance with a second embodiment of the present invention in a disassembled state. The same components as those in the first embodiment are represented by the same reference numerals. Thus, the description of the same components will not be repeated here.

In the second embodiment, the foremost end of a soft tube 1 is slantwise cut. Namely, the slantwise extending foremost surface of the soft tube 1 and a center axis of the assembly define an angle $\alpha$. In contrast with the first embodiment, the flange 4 is not formed with any projections. However, the fitting function of the assembly in accordance with the second embodiment is substantially the to that in the first embodiment of the present invention. Namely, as the soft tube 1 is fitted onto the fitting portion 3 of the hard member 2, the foremost end part of the soft tube 1 is increasingly deflexed along the side wall of the flange 4 while coming in close contact therewith. Therefore, tight fitting is achieved with the soft tube 1.

Figure 5:
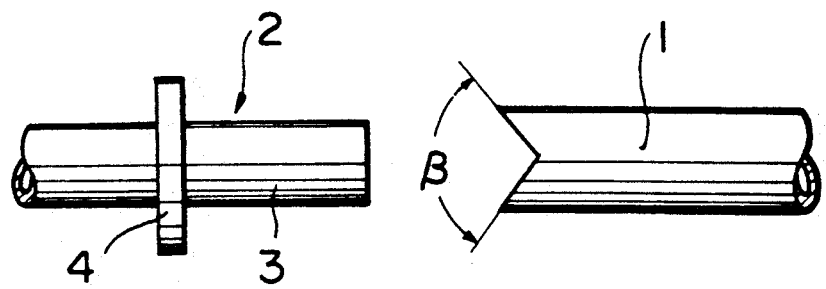
FIG. 5 is a side view of an assembly composed of a hard member and a soft tube fitted onto the hard member for a medical uses in accordance with a third embodiment of the present invention in a disassembled state.

FIG. 5 is a side view which illustrates an assembly composed of a hard member and a soft tube fitted onto the present invention. The same components as those in the first and second embodiments are likewise represented by the same reference numerals.

In this embodiment, the foremost end of a soft tube 1 is cut in a V-shaped contour as seen from the side symmetrically relative to a center axis of the soft tube 1 while defining an opening angle of $\beta$. The fitting function derived from the third embodiment is entirely the same as that in the second embodiment. Namely, as the soft tube 1 is fitted onto the fitting portion 3 of the hard member 2, the bifurcated foremost end parts of the soft tube 1 are increasingly deflexed along the side wall of the flange 4 while enlarging the opening angle $\beta$. Thus, increased liquidtightness and fitting function are attained with the assembly in accordance with the third embodiment of the present invention. In the third embodiment, two V-shaped cutouts are formed along the periphery of the soft tube 1 at the foremost end of the latter. Alternatively, three or more V-shaped cutouts may be formed on the foremost end surface of the soft tube 1 in a spaced relationship. In addition, the shape of each cutout need not be limited to a V-shaped contour. The number of cutouts, the size of each cutout and the shape of each cutout may be determined as desired.

It should be noted that a feature which the second and third embodiments of the present invention have in common is that a part or the whole part of the foremost end of the soft tube 1 does not extend in parallel with the side wall of the flange 4.

As will be readily apparent from the above description, the assembly of the present invention has advantageous effects in that a firm and reliable fitting function can be assured with a simple structure and therefore the assembly can easily be fabricated at inexpensive cost.

While the present invention has been described above with respect to three preferred embodiments thereof, it should of course be understood that the present invention should not be limited only to those embodiments but various changes or modifications may be made without departure from the scope of the invention as defined by the appended claims.

What is claimed is:

1. In an assembly composed of a hard member and a soft tube fitted onto said hard member for medical uses, said hard member being molded of hard synthetic resin and including a flange and a fitting portion onto which said soft tube is fitted and said soft tube being molded of soft synthetic resin, the improvement wherein:

said flange is formed with a plurality of wedge-shaped projections substantially shorter than said fitting portion which are arranged along a common circle in a spaced relationship, said projections projecting toward a foremost end of said soft tube and arranged to engage and compress the foremost end of said soft tube to firmly hold said soft tube between the projections and the fitting portion of the hard member in a clamped state when said soft tube is fitted onto the fitting portion of the hard member and the foremost end of the soft tube comes in close contact with a side wall of the flange of the hard member, said foremost end being held in said clamped state due to a force pressing said soft tube onto said flange resulting from the placement of said projections and said fitting portion only when a pressing force is present;

wherein said hard member, said flange and said projection are integrally formed as a single unit.

2. The assembly as claimed in claim 1, wherein the number of said projections is two.

3. The assembly as claimed in claim 1, wherein said hard member is made of polyethylene or polypropylene and said soft tube is made of polyvinylchloride.

* * * * *